United States Patent [19]

Diepenhorst et al.

[11] Patent Number: 5,073,647

[45] Date of Patent: Dec. 17, 1991

[54] REDUCTION AND INHIBITION OF ETU CONTENT IN ALKYLENEBISDITHIOCARBAMATES

[75] Inventors: Pieter C. Diepenhorst; Pieter Kool, both of Zuid-Holland; Jacobus A. M. Nouws, Etten-leur, all of Netherlands

[73] Assignee: Pennwalt France S.A., Plaisir, France

[21] Appl. No.: 513,735

[22] Filed: Apr. 24, 1990

[51] Int. Cl.$^5$ .................... C07C 61/00; C07C 333/00; A61K 31/21

[52] U.S. Cl. ........................ 562/27; 556/39; 558/235

[58] Field of Search ........................ 558/235; 562/27; 514/513; 556/39

[56] References Cited

U.S. PATENT DOCUMENTS

| | | | |
|---|---|---|---|
| 2,579,384 | 12/1951 | Handy et al. | 558/235 |
| 3,210,394 | 10/1965 | Nemec et al. | 558/235 |
| 3,379,610 | 4/1968 | Lyon et al. | 558/235 |
| 3,869,486 | 3/1975 | Van den Boogaart et al. | 558/235 |
| 4,217,293 | 8/1980 | Adams, Jr. | 558/235 |
| 4,344,890 | 8/1982 | Adams, Jr. | 558/235 |

FOREIGN PATENT DOCUMENTS

| | | | |
|---|---|---|---|
| 890669 | 2/1982 | Belgium | 558/235 |
| 0008533 | 3/1980 | European Pat. Off. | 558/235 |

*Primary Examiner*—Mary C. Lee
*Assistant Examiner*—Robert C. Whittenbaugh
*Attorney, Agent, or Firm*—Panitch Schwarze Jacobs & Nadel

[57] ABSTRACT

A method is provided for stabilizing alkylenebisdithiocarbamates (EBDC) by mixing the EBDC with chloralhydrate to reduce the content of alkylenethiourea (ETU) in the EBDC. The chloralhydrate is preferably added in an amount of about 0.1 to 5 weight percent based upon the EBDC. The preferably liquid (e.g., aqueous or alcoholic) reaction mixture is then preferably dried under vacuum. The stabilized EBDC product contains chloralhydrate, mono- and/or bis-trichloroethylol-alkylenethioureas, and less than about 0.015 weight percent ETU.

13 Claims, No Drawings

REDUCTION AND INHIBITION OF ETU CONTENT IN ALKYLENEBISDITHIOCARBAMATES

CROSS-REFERENCE TO RELATED APPLICATIONS

This application is related to our co-pending applications Ser. No. 492,526, filed Mar. 12, 1990 and Ser. No. 533,967, filed June 6, 1990, both directed to reduction and inhibition of ETU content in alkylenebisdithiocarbamates.

FIELD OF THE INVENTION

The present invention relates to the reduction and inhibition of the content of alkylenethiourea (imidazolidine-2-thiones) in alkylenebisdithiocarbamates. More particularly, the invention relates to the reduction of the content of ethylenethiourea (imidazolidine-2-thione or ETU) in 1,2-ethylenebisdithiocarbamates. The invention is directed to a method of obtaining and stabilizing the ETU content at very low levels, preferably less than 0.015 weight percent, in alkylenebisdithiocarbamate formulations.

BACKGROUND OF THE INVENTION

Various salts of 1,2-ethylenebisdithiocarbamic acid have been known for many years as agents for combating plant diseases caused by fungi. Among the ethylenebisdithiocarbamates (sometimes referred to as "EBDC") useful as plant fungicides are the manganese, zinc, nickel, cobalt, copper, sodium, potassium and ammonium salts of 1,2-ethylenebisdithiocarbamic acid or co-reacted metal EBDC. Preferred fungicides of this class are manganese EBDC (maneb), zinc EBDC (zineb), and particularly zinc coordination complexes of manganese EBDC (mancozeb).

A problem with the EBDCs is that they tend to degrade over time due to factors including oxidation, heat, humidity, etc., into, among other things, ethylenethiourea (imidazolidine-2-thione), commonly known as ETU. Due to this degradation, ETU content increases in concentration during storage of the EBDC. Since ETU has been found to have carcinogenic and teratogenic effects in laboratory animals, and no significant biological activity as a fungicide has been observed, ETU is an unwanted degradation product.

Over the years a number of processes and additives have been developed to reduce the ETU content of EBDCs. It is desirable that the ETU content of EBDC formulations be reduced to less than 0.015 percent by weight, based on the weight of the EBDC in the formulation. Several prior attempts have been made to reduce the content of ETU in EBDC by adding formaldehyde to the aqueous reaction mixture, preferably with a water-soluble zinc salt, and/or by optionally adding paraformaldehyde or another formaldehyde releasing agent (formaldehyde donor) to the dried product. See, for example, U.S. Pat. Nos. 4,217,293 and 4,344,890 of Adams. However, processes of reducing ETU content in EBDC are desired which result in lower ETU contents than obtained by using a formaldehyde donor.

SUMMARY OF THE INVENTION

According to the present invention, a method is provided for stabilizing alkylenebisdithiocarbamates by mixing with the EBDC an amount of chloralhydrate effective to reduce the content and inhibit the formation of ethylenethiourea in the EBDC. The chloralhydrate is preferably added in an amount of about 0.1 to 5 weight percent based on the weight of EBDC and may be added alone to undried EBDC or an aqueous formulation of EBDC, or may be added with water or another suitable solvent to dried EBDC. The stabilized product is then preferably vacuum dried and contains residual chloralhydrate, mono- and/or bis-trichloroethylōl-alkylenethioureas, and less than about 0.015 weight percent alkylenethiourea per se.

DETAILED DESCRIPTION OF PREFERRED EMBODIMENTS

Fungicidal salts of 1,2-ethylenebisdithiocarbamic acid are well known in the art and commercially available from a number of agricultural chemical companies, including Atochem North America, Inc. (formerly Pennwalt Corporation), Rohm & Haas Company, E.I. duPont de Nemours & Company, Roussel UCLAF, etc. Particularly preferred are the zinc and manganese coordination complexes of EBDC (mancozeb) which may be made by various processes, such as those described in U.S. Pat. Nos. 3,210,394; 3,379,610 and 3,869,486.

These fungicides are available in various forms, including aqueous liquid formulations (suspension concentrates, "SC") and dry wettable powders ("WP"). An example of one commercially available fungicide of this type is "PENNCOZEB" fungicide, which is a product available from Atochem North America, Inc. containing 80 percent active ingredient of a coordination product consisting of 16 percent manganese ions, 2 percent zinc ions, 62 percent ethylenebisdithiocarbamate ($C_4H_6N_2S_4$) ions and 20 percent inert ingredients.

However, it will be understood that the present invention is applicable to any alkylenebisdithiocarbamate, particularly 1,2-alkylenebisdithiocarbamates, which contains or yields ethylenethiourea (ETU) or ETU-like products as a degradation product. Other such alkylenebisdithiocarbamates, which can be considered as homologues of ethylenebisdithiocarbamates, include propineb (zinc 1-methyl-1,2-ethylenebisdithiocarbamate) which produces methyl-ETU, and metiram (zineb-ethylene thiuram disulfide adduct). For ease of reference herein, all of the alkylenebisdithiocarbamates and homologues which contain or yield ETUs will be referred to as "EBDCs." Similarly, all alkylenethioureas or like products will be referred to herein as "ETUs."

The present invention is based upon the reaction of ETU with chloralhydrate ($CCl_3CH(OH)_2$) in a liquid medium and/or in dried product. The mixing can be provided in any of a number of ways, including, for example:

(1) chloralhydrate may be added to the undried EBDC product, which is generally an aqueous paste (about 25 percent water) obtained from the reaction mixture for forming the EBDC;

(2) the chloralhydrate may be added by blending with the dried EBDC;

(3) the chloralhydrate may be added by means of a suitable solvent, such as water or ethanol, to the dried EBDC; or (4) the chloralhydrate may be added alone to liquid aqueous formulations containing the EBDC. Other possibilities will be evident to those skilled in the art based upon the present disclosure.

The chloralhydrate is mixed with the EBDC in an amount sufficient to react with any ETU which may be present in the EBDC or which is likely to be formed as the EBDC degrades during the normal storage life of the EBDC product. Amounts of chloralhydrate in the range of about 0.1 to 5 weight percent based upon the weight of EBDC have been found to be satisfactory according to the present invention, and about 1 weight percent is generally sufficient.

To facilitate distribution of the chloralhydrate throughout the EBDC formulation, so that it will be available for further reaction with ETU during storage, an appropriate solvent such as water or ethanol is added in an amount sufficient to homogenize the product well. At least 200 weight percent of solvent (preferably water) based on the weight of EBDC is preferred. The solvents need only to remain for sufficient time to obtain a good dispersion of the chloralhydrate with the EBDC. Thereafter, the mixture is dried, preferably under vacuum, to a powder. It is also possible to leave the EBDC undried as an aqueous formulation. In either event, oxygen, and high temperatures should be avoided during drying and storage due to their degradative effects on the EBDC.

The method of the present invention may be illustrated by the following reaction equations. First, the chloralhydrate is in equilibrium with the non-hydrolysed corresponding aldehyde 2,2,2-trichloroethanal, as shown in equation I below:

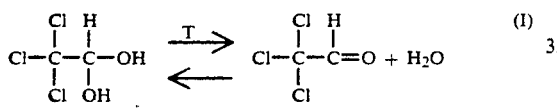

(I)

In the above equation I, room temperature is sufficient heat (T) to drive the reaction equation to the right. Next, this trichloroethanal can react with ETU to form the mono- and/or bistrichloroethylol-ethylenethioureas, namely N-(2,2,2-trichloro-1-hydroxyethyl)ethylenethiourea as shown in equation II below:

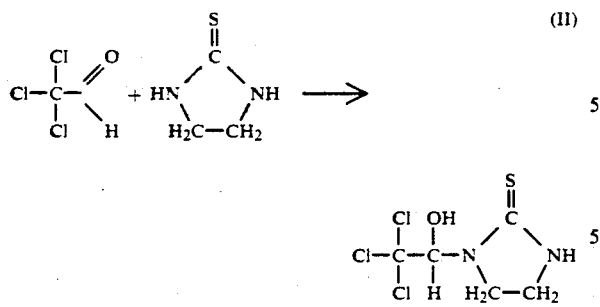

(II)

and N,N'-bis(2,2,2-trichloro-1-hydroxyethyl)ethylenethiourea, as shown in equation III below:

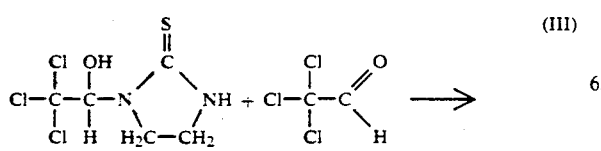

(III)

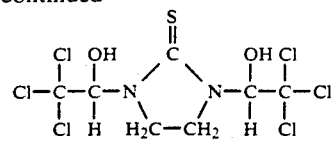

It goes without saying that anhydrous chloral (2,2,2-trichloroethanal) itself and other donors like chloral alcoholate show the same reactions.

Residual chloralhydrate facilitates the inhibition of the ETU content during storage. As a result, the stabilized alkylenebisdithiocarbamates according to the present invention will contain unreacted or residual chloralhydrate, mono-and/or bis-trichloroethylol-alkylenethioureas, and less than about 0.015 weight percent alkylenethiourea (ETU) per se based on the weight of the EBDC.

The present invention will now be described with further reference to the following specific, non-limiting example:

To 4 grams of mancozeb (PENNCOZEB), initially containing 0.05 weight percent of ETU, were added 35 milligrams of chloralhydrate and 10 ml of water. After stirring for 5 minutes, the wet paste was dried in a vacuum (9 mm Hg for 16 hours) affording a product with a water content of 0.5%. Within 14 days of storage an ETU content of 0.015 weight percent was reached, and after 50 days an ETU content of 0.010 weight percent was reached and stayed unchanged for at least 226 days.

In contrast, for a PENNCOZEB sample without the addition of stabilizer the ETU content was 0.11% weight percent directly and increased first to 0.14% after 31 days and further to 0.19% after 92 days. For mancozeb sample dried with 0.5% formaldehyde the ETU content was directly 0.16% and increased first to 0.054% after 31 days and further to 0.098% after 92 days.

The present invention is advantageous over the use of formaldehyde donor in several respects. First of all, formaldehyde is a gas which can escape very easily from the EBDC without reaction. Secondly, chloralhydrate is a solid which slowly releases the corresponding aldehyde, decreasing ETU concentration during storage and inhibiting the formation of ETU for a longer time.

The present invention may be embodied in other specific forms without departing from the spirit or essential attributes thereof and, accordingly, reference should be made to the appended claims, rather than to the foregoing specification as indicating the scope of the invention.

We claim:

1. A method of stabilizing alkylenebisdithiocarbamates (EBDC), the EBDC consisting essentially of a metal salt or coordination complex of an alkylenebisdithiocarbamic acid, comprising mixing with the EBDC an amount of chloralkydrate effective to reduce the content of alkylenethiourea in the EBDC.

2. A method according to claim 1 wherein said EBDC is 1,2-ethylenebisdithiocarbamate.

3. A method according to claim 2 wherein the cation of the metal salt or coordination complex is selected from the group consisting of manganese, zinc, nickel, cobalt, copper, sodium, potassium, ammonium and co-reacted complexes thereof.

4. A method according to claim 3 wherein the metal salt or coordination complex is a co-reacted complex with manganese and zinc.

5. A method according to claim 1 wherein the chloralhydrate is mixed in an amount of about 0.1 to 5 weight percent based on the EDBC.

6. A method according to claim 1 wherein the chloralhydrate is mixed with an undried EBDC.

7. A method according to claim 1 wherein water and chloralhydrate are mixed with the EBDC.

8. A method according to claim 7 wherein water is present in an amount of at least 200 weight percent based on the EBDC.

9. A method according to claim 1 wherein chloralhydrate is mixed with an aqueous formulation of the EBDC.

10. A method according to claim 1 wherein the mixture is subsequently dried to a powder.

11. A method according to claim 10 wherein the mixture is vacuum dried.

12. A stabilized alkylenebisdithiocarbamate consisting essentially of a metal salt or coordination complex of an alkylenebisdithiocarbamic acid, containing chloralhydrate, mono- and/or bis-trichloro-ethylol-alkylenethioureas, and less than about 0.015 weight percent alkylenethiourea per se based on the weight of the alkylenebisdithiocarbamate.

13. A stabilized product according to claim 12 wherein said alkylenebisdithiocarbamate is 1,2-ethylenebisdithiocarbamate.

* * * * *